(12) United States Patent
Sliwa et al.

(10) Patent No.: US 10,561,395 B2
(45) Date of Patent: Feb. 18, 2020

(54) FORCE-SENSING ABLATION CATHETER

(71) Applicant: St. Jude Medical, Cardiology Division, Inc., St. Paul, MN (US)

(72) Inventors: John W. Sliwa, Los Alto Hills, CA (US); Stephen A. Morse, Menlo Park, CA (US); Zhenyi Ma, San Jose, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1121 days.

(21) Appl. No.: 14/214,616

(22) Filed: Mar. 14, 2014

(65) Prior Publication Data

US 2014/0276006 A1 Sep. 18, 2014

Related U.S. Application Data

(60) Provisional application No. 61/800,256, filed on Mar. 15, 2013.

(51) Int. Cl.
*A61B 8/08* (2006.01)

(52) U.S. Cl.
CPC .................................. *A61B 8/0841* (2013.01)

(58) Field of Classification Search
CPC ...................... A61B 18/1492; A61B 2090/065
See application file for complete search history.

(56) References Cited

U.S. PATENT DOCUMENTS

| 4,551,826 | A | * | 11/1985 | Kritz ..................... G10K 11/30 |
| | | | | 310/335 |
| 4,949,321 | A | | 8/1990 | Magori |
| 6,436,108 | B1 | | 8/2002 | Mears |
| 2007/0282211 | A1 | * | 12/2007 | Ofek .................... A61B 5/0215 |
| | | | | 600/523 |
| 2009/0099551 | A1 | * | 4/2009 | Tung ..................... A61B 5/103 |
| | | | | 604/530 |
| 2010/0298826 | A1 | | 11/2010 | Leo et al. |
| 2011/0144491 | A1 | | 6/2011 | Sliwa et al. |

(Continued)

FOREIGN PATENT DOCUMENTS

| EP | 2477572 B1 | 1/2013 |
| WO | 2011/033421 A1 | 3/2011 |

(Continued)

OTHER PUBLICATIONS

International Search Report and Written Opinion (PCT/US2014/02985); ISA: European Patent Office; dated Aug. 21, 2014.

*Primary Examiner* — Jeffrey G Hoekstra
*Assistant Examiner* — Jason M Ip
(74) *Attorney, Agent, or Firm* — Dykema Gossett PLLC

(57) ABSTRACT

A force-sensing tip assembly for a catheter comprises a tip shell, an acoustic transducer, a first target, and a first spring. The tip shell is for joining to the catheter. The acoustic transducer is disposed within the tip shell and is capable of generating an acoustic ping. The first target is spaced from the acoustic transducer within the tip shell. The first spring is in the tip shell and configured to allow a relative position between the acoustic transducer and the first target to change over a range. The first target is shaped and positioned to reflect at least a portion of the acoustic ping back to the acoustic transducer as a first echo over at least a portion of the range.

22 Claims, 10 Drawing Sheets

(56) References Cited

U.S. PATENT DOCUMENTS

| | | |
|---|---|---|
| 2011/0313417 A1 | 12/2011 | De La Rama et al. |
| 2012/0165669 A1* | 6/2012 | Barley .......................... 600/439 |
| 2012/0253167 A1* | 10/2012 | Bonyak .................. A61B 5/06 |
| | | 600/409 |
| 2012/0265069 A1 | 10/2012 | Sliwa et al. |
| 2012/0265070 A1 | 10/2012 | Sliwa et al. |
| 2012/0265184 A1 | 10/2012 | Sliwa et al. |
| 2012/0302877 A1 | 11/2012 | Harks et al. |
| 2014/0018665 A1 | 1/2014 | Meredith |

FOREIGN PATENT DOCUMENTS

| | | |
|---|---|---|
| WO | 2013/014583 A1 | 1/2013 |
| WO | 2013/162765 A1 | 10/2013 |

* cited by examiner

FORCE-SENSING ABLATION CATHETER

BACKGROUND OF THE INVENTION a. Field of the Invention

The present disclosure relates generally to medical devices having force-sensing capabilities. More particularly, the instant disclosure relates to force-sensing catheters.

b. Background Art

Electrophysiology catheters are used in a variety of diagnostic, therapeutic, and/or mapping and ablative procedures to diagnose and/or correct conditions such as atrial arrhythmias, including, for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed into vasculature of a patient via a percutaneous approach, such as through a femoral or subclavian artery. The catheter is advanced through the vasculature to an intended site, for example, a site within the heart of the patient. The catheter may carry one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. This lesion disrupts undesirable cardiac activation pathways and thereby limits, corrals, or prevents errant conduction signals that can form the basis for arrhythmias.

In order to advance a distal tip of the catheter through the vasculature, a clinician may manipulate a proximal end of the catheter by sequentially or simultaneously applying torque, and longitudinal or axil pushing force. The distal tip of the catheter may also be selectively deflected or rotated in a desired direction if the catheter is steerable from the proximal end. It can be difficult to manipulate catheters in this manner, and it can be important to have a reliable indication of the force being applied to the cardiac tissue via this manipulation of the catheter. During an ablative procedure, the amount of pressure being applied to the tissue can influence the outcome of the procedure and/or the amount of time required to complete a procedure. Also, there may be some safety advantages to knowing how much pressure the catheter is applying to the cardiac tissue.

An exemplary known force-sensing catheter is described in U.S. patent application Ser. No. 13/547,397 to Meredith. Such a catheter includes a force-sensing tip having a spring aligned along the axis of the catheter that deflects under pressure. Movement of the spring is determined by following movement of tracker coils within the catheter tip, before and after deflection of the mechanical spring, using a magnetic resonance imaging (MRI) system. The distance traversed by the tracker coils is converted to the distance of compression of the mechanical spring, which is then used to determine the force applied to the catheter tip using the axial spring constant of the mechanical spring. Such a catheter, however, only measures axial force applied by the tip. Furthermore, the catheter requires an external imaging system to follow the location of the tracker coils in order to determine force.

BRIEF SUMMARY OF THE INVENTION

The present disclosure is directed to tip assemblies for catheters that are capable of generating measurements that can be used to provide an indication of the force with which the tip is being applied to a body, such as tissue. The force-sensing tips of the present disclosure provide omni-directional force measurements, e.g. axial and bending force, applied by the tip. Furthermore, the force-sensing tips of the present disclosure are self-contained in that all measurements for determining force applied by the tip can be obtained from within the tip itself, without the need for external measurements from an imaging system or the like.

In one embodiment, a force-sensing tip assembly for a catheter comprises a tip shell, an acoustic transducer, a first target, and a first spring. The tip shell is for joining to the catheter. The acoustic transducer is disposed within the tip shell and is capable of generating an acoustic ping. The first target is spaced from the acoustic transducer within the tip shell. The first spring is in the tip shell and configured to allow a relative position between the acoustic transducer and the first target to change over a range. The first target is shaped and positioned to reflect at least a portion of the acoustic ping back to the acoustic transducer as a first echo over at least a portion of the range.

In one embodiment, a medical device system comprises a catheter shaft, a force-sensing tip assembly, and a control system. The catheter shaft has a proximal region and a distal region. The force-sensing tip assembly is disposed at the distal region of the catheter shaft. The force-sensing tip assembly comprises a tip shell, an acoustic transducer, a first target, and a first spring. The tip shell is joined to the catheter shaft. The acoustic transducer is disposed within the tip shell and is capable of generating and receiving an acoustic ping. The first target is spaced from the acoustic transducer within the tip shell to deflect the acoustic ping as a first reflected acoustic echo back to the acoustic transducer. The first spring is joined to the tip shell, and is configured to allow a relative position between the acoustic transducer and the first target to change by deflection of the spring. The control system is connected to the force-sensing tip via the catheter shaft, and is configured to analyze changes in the first acoustic echo to determine a force generated by the first spring.

DETAILED DESCRIPTION OF THE INVENTION

Various representative embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Figure 1A:
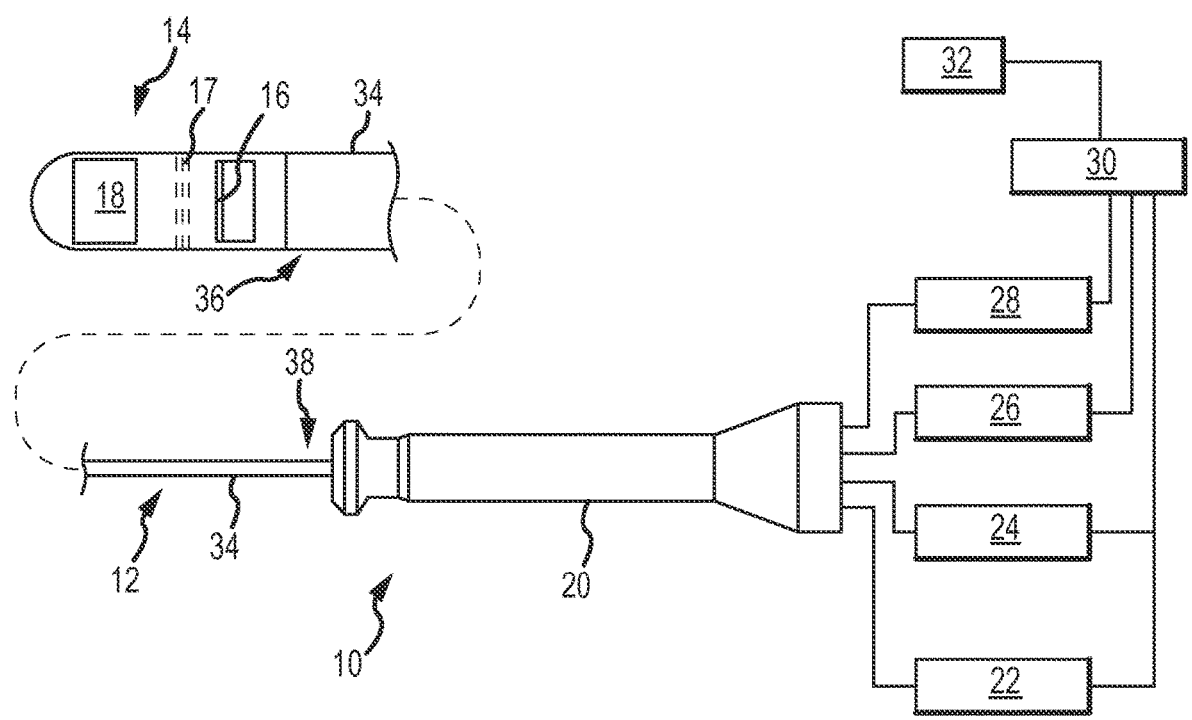
FIG. 1A is a schematic diagram of a medical device system incorporating an ablation catheter with a force-sensing tip.

FIG. 1A is a schematic diagram of medical device system 10 incorporating ablation catheter 12 with force-sensing tip 14. In FIG. 1, force-sensing tip 14 is illustrated as being enlarged to show acoustic transducer 16, spring 17 and target 18. Medical device system 10 also includes control handle 20, which is connected to analyzer 22, acoustic energy driver 24, ablation energy driver 26, and fluid source 28. Control unit 30 is in communication with analyzer 22, energy drivers 24 and 26, fluid source 28, and user interface 32. Catheter 12 includes elongate catheter body 34, to which is connected force-sensing tip 14 at distal region 36, and handle 20 at proximate region 38. This disclosure describes a force-sensing tip that, in one embodiment, reports to an operator of the system the bending and axial force components of the total force upon the tip using pulse-echo principles.

Catheter 12 is connected to ablation energy driver 26 to provide an ablation activation to tip 14. In one embodiment, ablation energy driver 26 may comprise a radio frequency (RF) generator. Catheter 12 and/or tip 14 may include one or more electrodes (not shown) to facilitate ablation and location of catheter 12, such as with the aid of a magnetic-based or voltage-based imaging systems. Furthermore, catheter 12 may be outfitted with any number of alternative or additional ablating and imaging technologies, such as sonographic imaging and high-intensity focused ultrasound (HIFU) ablating systems. Fluid source 28 provides an irrigation fluid, such as saline, to catheter 12 in order to, among other things, provide cooling to tip 14 and to provide a low-loss path for ultrasonics to propagate within the tip.

Catheter 12 is also connected to acoustic energy driver 24 to provide acoustic pinging energy to acoustic transducer 16. In one embodiment, acoustic energy driver 24 may comprise an ultrasonic pulser. As will be described in greater detail below, variations in the pinging energy waveform from acoustic transducer 16 after reflection, or echo, from target 18 due to deflection of tip 14 at spring 17 can be used to determine the force with which tip 14 is pushed against an object, such as tissue within an organ of a patient.

Using handle 20, catheter 12 is fed into an organ, such as the heart of a human, in order to perform various mapping, imaging, diagnostic and/or surgical procedures. For example, catheter 12 can be used to ablate tissue within the heart to, among other things, influence the path of electrical current through the heart. Control unit 30 controls the acoustic and ablation energy from acoustic energy driver 24 and ablation energy driver 26, respectively, during operation of system 10. For example, control unit 30 is configured to carry out duty cycles, e.g. frequency and amplitude, for the application of ablation and transmitted and received pinging energy. Control unit 30 may be manually operated or automatically operated to control ablation and pinging as desired by the operator.

Analyzer 22 conditions and analyzes pinging echo data collected by acoustic transducer 16 within tip 14 to determine a change in position of target 18. The collected data can be used to determine the contact force of tip 14 based on, for example, a known relationship to one or more spring constants of spring 17 in distal region 36. Control unit 30 and/or analyzer 22 may perform other functions with the collected data, such as filtering, sorting, storing and the like. Information relating to the force applied by tip 14 is presented to an operator of system 10 at user interface 32. In one embodiment, real time assessment of the applied force can be presented on a graphical user interface within user interface 32.

Figure 1B:
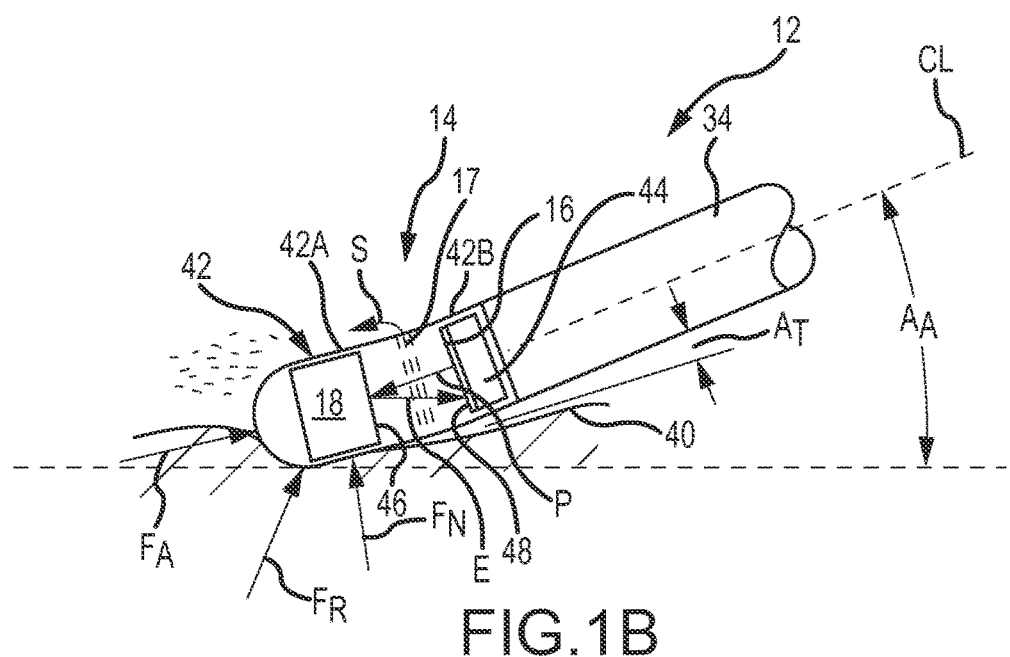
FIG. 1B is a schematic diagram of the ablation catheter of FIG. 1A illustrating the force-sensing tip being deflected via contact with tissue so as to change a position of an acoustic target relative to an acoustic transducer.

FIG. 1B is a schematic diagram of ablation catheter 12 of FIG. 1A illustrating force-sensing tip 14 being deflected via contact with tissue 40 so as to change a position of target 18 relative to acoustic transducer 16. Tip 14 also includes tip shell 42, which connects to catheter body 34. Spring 17 separates tip shell 42 into distal portion 42A and proximal portion 42B. Transducer 16 is mounted on backer 44. Fluid, such as saline S, is discharged from tip 14 through appropriate porting.

Catheter body 34 comprises an elongate hollow tube or shaft, also known as a lumen, that connects tip shell 42 and handle 20 (FIG. 1). Catheter body 34 extends along center line CL. In various embodiments, catheter body 34 is flexible so as to allow steering and deflection of tip 14. Tip shell 42 comprises a hollowed-out body into which various components of tip 14 are mounted. Tip shell 42 may be fabricated from any material suitable for use in medical device systems, such as polymers, metals and metal alloys. In one embodiment, tip shell 42 is fabricated from nitinol (nickel titanium alloy). Likewise, catheter body 34 may be fabricated from any suitable material. Tip shell 42 may be joined to catheter body 34 via any suitable method, such as welding, threaded engagement or adhesive. If tip shell 42 is to act as an RF ablator of tissue, it is made of an electrical conductor, such as a known platinum-iridium tip alloy.

Tip shell 42 houses acoustic transducer 16 and target 18. Additionally, although not illustrated in FIG. 1B, tip shell may house other components of medical device system 10, such as components for performing ablation and locating of tip 14. Acoustic transducer 16 is electrically coupled to components of medical device system 10, such as acoustic energy driver 24 (FIG. 1A), via wires (not shown) extending through catheter body 34. Target 18 is disposed within tip shell 42 with a line of sight of transducer 16 in order to allow acoustic signals to travel between transducer 16 and target 18 while spring 17 is at rest and over at least a portion of a range of movement of spring 17. Both acoustic transducer 16 and target 18 are disposed within tip shell 42 so as to not interfere with operation of other functions of tip 14, such as ablating, locating and irrigating functions.

In the disclosed embodiment, backer 44 is mounted to tip shell 42 near catheter body 34, while target 18 is mounted to tip shell 42 near the very distal end of tip 14. As such, wiring for transducer 16 need not extend all the way through tip shell 42 and across spring 17. Backer 44 comprises any suitable piece of supporting attenuating material upon which acoustic transducer 16 may be mounted. For example, a non-porous piezoresistive transducer 16 may be mounted on a tungsten-loaded epoxy backer 44. Backer 44 is joined to tip 14 by any suitable means, such as via projections (not shown) spaced intermittently around the circumference of backer 44 to join with tip shell 42. Target 18 may be similarly mounted within tip shell 42. As such, fluid and wiring from handle 20 (FIG. 1A) is permitted to pass around acoustic transducer 16 and target 18 between the projections. For example, saline S from fluid source 28 (FIG. 1A) can be delivered to tip 14 via appropriate fluid passages (not shown) extending through catheter body 34. Saline S may be discharged from tip 14 through dedicated porting (not shown) or openings in tip shell 42 concurrent in the geometry of spring 17.

Spring 17 is provided in tip shell 42 to allow relative displacement between transducer 16 and target 18. Spring 17 is disposed between acoustic transducer 16 and target 18. Thus, proximal section 42B and transducer 16 remain stationary with respect to catheter body 34, while distal section 42A and target 18 are moveable relative to catheter body 34. Although, in other embodiments, spring 17 may be located in other positions that allow target 18 to be moved with respect to transducer 16. For example, spring 17 may be located concentric with either transducer 16 and target 18, or fore or aft of transducer 16 or target 18. Spring 17 comprises a flexible, hinge-like member that allows tip shell 42 to change shape. In the embodiment of FIG. 1B, spring 17 comprises a laser slotting of tip shell 42 that allows tip shell 42 to elongate and contract along centerline CL, and that allows distal portion 42A to be displaced angularly and/or axially from or along centerline CL relative to proximal portion 42B an amount equal to tilt angle $A_T$. Mechanical properties of spring 17, such as bending spring constant and axial spring constant, are stored in control unit 30 for analysis by analyzer 22 (FIG. 1A) in conjunction with acoustic echo data collected by transducer 16 or by a CPU within control unit 30 itself. Various embodiments of spring 17 are discussed in greater detail with reference to FIG. 5.

Acoustic transducer 16 emits acoustic ping P, which is reflected back to transducer 16 as acoustic echo E by target 18. Acoustic transducer 16 may comprise any suitable transducer capable of emitting a signal, such as a sound wave, that can be detected upon being reflected back to the transducer, as are known in the art. Suitable transducers include piezotranducers, capacitive micro-machined ultrasonic transducers (CMUTs), all-ceramic piezotranducers, sol-gel piezotransducers and piezocomposite piezotransducers. As such, acoustic transducer 16 may include separate emitter and receiver components, although simplified as a single component in the present disclosure.

Target 18 comprises an object that is capable of reflecting acoustic ping P back to transducer 16 to generate echo E. Although not necessary, it is preferable that target 18 have a highly reflective surface, such as a mirrored surface. In one embodiment, target 18 comprises a metallic mirror, such as a polished stainless steel mirror. In order to reduce weight, target 18 may comprise a thin reflective surface backed by a microsphere-filled polymer. The path between transducer 16 and target 18 may be filled with fluid, such as saline S, in order to facilitate acoustic transmission and to preclude formation of blocking bubbles within the tip.

Due to the presence of spring 17, target 18 is able to move with respect to acoustic transducer 16 when a force is applied to distal portion 42A of tip shell 42. For example, as catheter 12 contacts tissue 40 at approach angle $A_A$, resultant force $F_R$ acts against tip 14. Force $F_R$ causes distal section 42A of tip shell 42 to deflect with respect to proximal section 42B an amount equal to tilt angle $A_T$. Force $F_R$ also causes distal section 42A of tip shell 42 to translate closer to proximal section 42B along centerline CL. Thus, resultant force $F_R$ can be broken down into constituent vector components: normal force $F_N$ and axial force $F_A$. In the illustrated embodiment, normal force $F_N$ causes spring 17 to radially bend, while axial force $F_A$ causes spring 17 to axially compress. Analysis in the change of the waveform timing, amplitude and shape of echo E due to these movements can be used to determine the distance and/or angle that target 18 has traversed, which can then be converted into a force measurement using known or pre-determined mechanical characteristics of spring 17.

Acoustic transducer 16 fires acoustic ping P towards target 18. Acoustic ping P is emitted from transducer 16 as a symmetrical beam about the center of transducer 16, which coincides with centerline CL in the illustrated embodiment. The beam for acoustic ping P is most intense at its center and becomes less intense further away from the center.

When the tip is unloaded, transducer 16 and target 18 are disposed in a known orientation and distance such that the time it takes ping P to reach target 18 and for echo E to return and its echo amplitude are known. Thus, when undeflected, as in the embodiment of FIG. 1B, reflective surface 46 of target 18 and emitting surface 48 of transducer 16 are approximately parallel and spaced across a known distance. Also, the amplitude and intensity (total energy) of echo E is known, as is dictated by acoustic energy driver 24 and control unit 30 and the rest angle of the target 18, which can be orthogonal at rest.

As echo E changes with a change in spatial relationship between transducer 16 and target 18, the change in deflection of tip 14 can be determined via waveform analysis of echo E. The deflection of tip 14 can be converted into axial force $F_A$ and normal force $F_N$ using the axial and bending spring constants of spring 17. Thus, acoustic receiver or analyzer 22 (FIG. 1A) includes a detector that is capable of measuring the intensity (e.g. amplitude) of a reflected waveform as well as being capable of determining time intervals (e.g. phase shifting) between reflected waveforms. Analyzer 22 and control unit 30 (FIG. 1A) are capable of analyzing data collected by transducer 16 to perform the appropriate conversion of waveform data to force data. For example, the calculated change in position of target 18 may be used to analyze Hooke's Law, F=kX, where F is force, k is a spring constant, and X is a distance that the spring is deflected. In the embodiment of FIG. 1B, analysis of only a single waveform is used to produce a comingled, or coupled, force measurement that indicates the combined force applied to tip 14. Specifically, amplitude and phase-shift data from a single target echo waveform is used to produce both normal force $F_N$ and axial force $F_A$ measurements. Such an arrangement is operable because the echo delay due to axial deflection is relatively independent of the echo broadening due to angulation deflection. However, further accuracy may be obtained from the angular phase information of the ultrasonic echo to deduce one or both of axial distance and angular orientation.

If distal portion 42A is not deflected such that tilt angle $A_T$ is zero, i.e. spring 17 is left in an un-stressed state as shown in FIG. 1A, acoustic ping P travels approximately straight towards target 18 and echo E travels straight back to transducer 16 along the same centerline. In such case, echo E has the maximum possible amplitude, which will be approximately the same amplitude as ping P, setting aside losses from scattering, diffraction and the like. As distal portion 42A becomes displaced such that tilt angle $A_T$ is not zero, i.e. spring 17 is in a stressed state as shown in FIG. 1B, echo E will be angled relative to emitting surface 48. The amplitude of echo E will drop as some of the intensity of acoustic ping is directed off of transducer 16. Amplitude will fall off uniformly regardless of the direction of tilt, if transducer 16 is round. Furthermore, the returned waveform, whatever portion makes it back to transducer 16, will be predictably broadened. The diameters of transducer 16 and target 18 can be varied to manipulate the amplitude falloff from bending deformation in order to achieve higher signal resolution. If distal portion 42A becomes angled past a threshold level, echo E will not be detected by transducer 16. Thus, the configuration of FIG. 1B is particularly well suited for low tilt angles $A_T$. However, spring 17 may be outfitted with stops (discussed in greater detail with reference to FIG. 5) that prevent distal portion 42A from deflecting beyond a particular tilt angle $A_T$. A given design may or may not allow echoes to be returned off the edges of transducer 16. If the echoes are allowed to fall off the edges of transducer 16, reflection off of the interior walls of tip 14 as a wall-bounce should either be accounted for or avoided. One way to account for wall-bounce of echoes is to coat the interior walls and surfaces of tip 14, such as the interior of tip shell 42A, with a lossy or scattering material to minimize such wall-reflected signals.

Any bending of distal portion 42A inherently produces axial displacement of distal portion 42A even if no separate normal force $F_N$ is applied. However, in practice, at least a nominal amount of normal force $F_N$ will typically be applied by an operator of system 10. Axial displacement of distal portion 42A changes the amount of time that echo E takes to return to transducer 16. This change in time will show up as a phase-shift in echo E as compared to echo E of an un-deflected distal portion 42A (e.g. as is shown in FIG. 1A). Because the bending force will dominate the change in echo E, the embodiment of FIG. 1B is more sensitive to normal force $F_N$. Thus, the embodiment of FIG. 1B provides accurate normal force $F_N$ indication for low approach angles $A_A$ (e.g., approximately 0 to approximately 30 degrees), and accurate axial force $F_A$ indication for high approach angles $A_A$ (e.g. dot type lesioning at approximately 50 to approximately 90 degrees).

In order to perform adequate ablation techniques, it has been found that at least approximately 20 grams of normal force and approximately 400 gram-seconds of integrated ablation-force is desirable to form a good lesion, assuming adequate power and electrical contact. Thus, it is desirable to be able to provide to a physician operating system 10 an indication of the force with which tip 14 is being applied to tissue 40. Spring 17 is configured to be stiff relative to the force desired to perform ablation. For example, the maximum force needed to deflect distal portion 42A a few degrees or less at tilt angle $A_T$ is approximately 80 grams to approximately 100 grams, in one embodiment. Thus, adequate ablation forces (e.g. 20-40 grams) will only produce a small amount of deflection of the tip, such as to not unduly interfere with the catheter procedure. This also permits enough deflection of distal portion 42A to detect force $F_R$ via waveform analysis, but not enough for reflections of echo E to completely drop off of transducer 16. Force-sensing tip 14 provides an operator of system 10 with an indication of how much force tip 14 is applying to tissue 40 to ensure adequate ablation without risking damage of tissue 40.

Figure 1C:
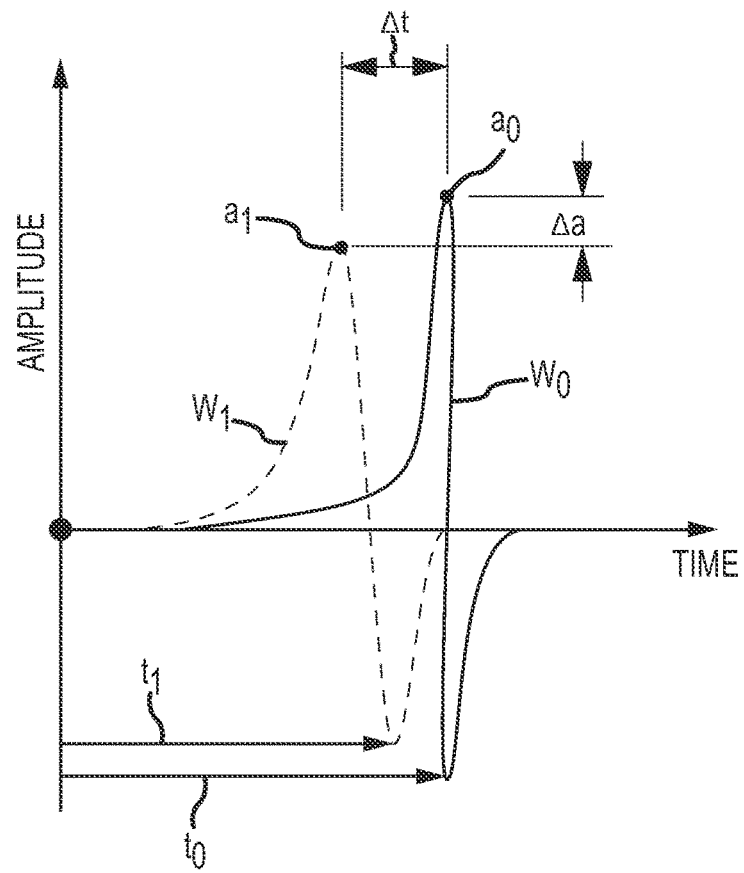
FIG. 1C is a graph illustrating the behavior of a pulse-echo waveform from the acoustic transducer of FIGS. 1A and 1B before and after deflection of the acoustic target.

FIG. 1C is a graph illustrating the behavior of the waveform of echo E from acoustic transducer 16 of FIGS. 1A and 1B before and after deflection of force-sensing tip 14. Waveform $W_0$ depicts echo E for tip 14 under no load, such as would be generated in FIG. 1A. Waveform $W_1$ depicts echo E for tip 14 under axial and bending load, such as would be generated in FIG. 1B. Waveform $W_o$ is the undeflected baseline of echo E received by transducer 16 for the ping P generated by transducer 16 for a given set of inputs from acoustic energy driver 24. Waveform $W_o$ has a given amplitude $a_0$ and phase $t_0$, while waveform $W_1$ has a given amplitude $a_1$ and phase $t_1$. Note also that reflected wave $W_1$ is broader in time due to the angulation.

Axial deflection of target 18 with distal portion 42A causes a change in the phase, $\Delta t$, of echo E. As can be seen in FIG. 1B, under axial compressive force from axial force $F_A$, target 18 moves closer to transducer 16 and the time it takes for echo E to return to transducer 16 is reduced. Thus, waveform $W_1$ undergoes a phase shift to the left in FIG. 1C, indicating shorter travel time of echo E. An axial tensile load would shift waveform $W_1$ to the right in FIG. 1C as the travel time for echo E to return to transducer 16 would increase. Thus, a pure axial displacement of tip 14 would result in only a phase change, $\Delta t$.

Bending deflection of target 18 with distal portion 42A causes a change in the amplitude, $\Delta a$, of echo E accompanied by peak broadening. As can be seen in FIG. 1B, under bending force from normal force $F_N$, surface 46 of target 18 becomes angled with reference to surface 48 of transducer 16 and echo E is angled closer to the edge of transducer 16, which directs more of the intensity of echo E off of transducer 16. Thus, waveform $W_1$ undergoes an amplitude reduction inward in FIG. 1C, indicating that less total energy from echo E is impacting transducer 16. Waveform $W_1$ would undergo an amplitude reduction from waveform $E_0$ for bending in any radial direction of tip 14 due to symmetry of transducer 16, target 18 and ping P. Thus, a pure bending displacement of tip 14 would result in only an amplitude reduction $\Delta a$ with its accompanying peak broadening. However, as indicated above, actual bending of tip 14 would incur some axial compression.

In order to generate waveforms $W_0$ and $W_1$, transducer 16 is typically fired repeatedly, approximately at least 4 times in 5 milliseconds, to obtain a numerical average of the several readings, thus reducing noise and improving the signal to noise (S/N) ratio of a single force reading.

It will be recognized that heart beat related anatomical motions also cause time-wise force variations over times much longer than 5 milliseconds such that heart motion can be seen in the time-wise force signal. Preferably, transducer 16 has a relatively high frequency such that axial resolution (and therefore force via deflection resolution) is acceptable. Transducer 16 operates at 10 Mhz or above, more preferably in the 20-30 Mhz range, and most preferably in the 35-50 Mhz range.

Waveform $W_1$ provides a single, combined indication of the total force being applied to tip 14. The amplitude change $\Delta a$ and accompanying peak broadening provide an indication of normal force $F_N$, while phase change $\Delta t$ provides an indication of axial force $F_A$. In other embodiments, separate waveforms can be provided from separate targets to even better provide decoupled normal and axial force indications. As such, each waveform can be manipulated upon deflection of separate targets to achieve higher resolution for axial and bending force analysis.

Figure 2A:
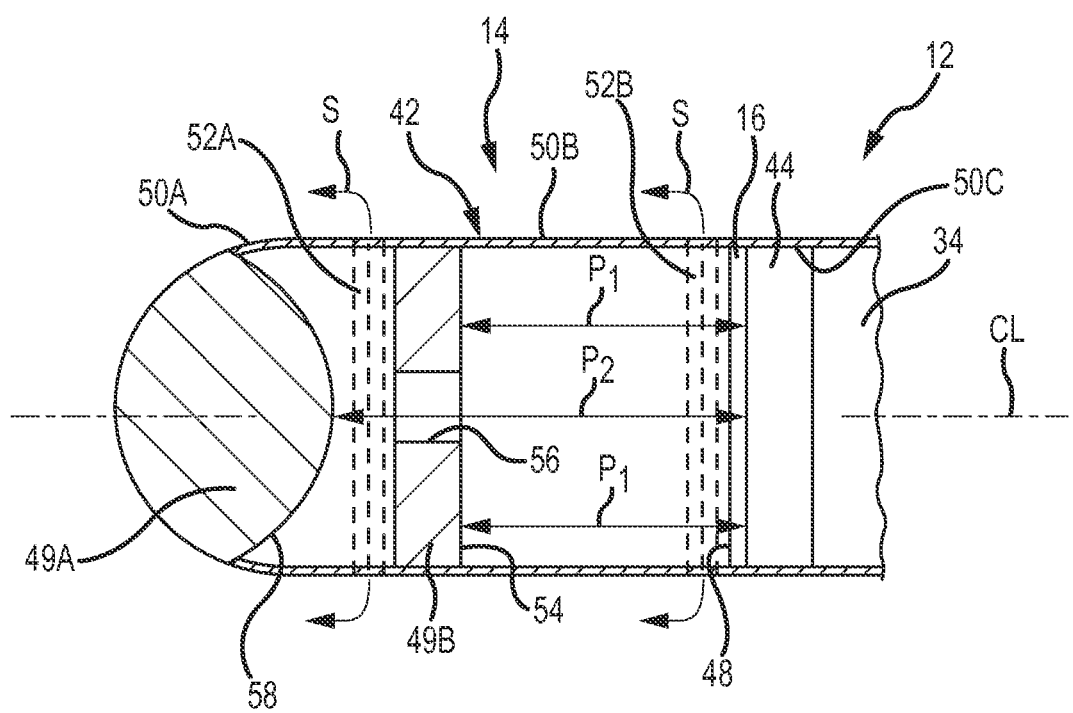
FIG. 2A is a schematic diagram of another embodiment of an ablation catheter with a force-sensing tip incorporating separate acoustic targets for axial and bending force measurements.

FIG. 2A is a schematic diagram of another embodiment of ablation catheter 12 with force-sensing tip 14 incorporating separate axial and bending force echo targets 49A and 49B, respectively. Tip 14 includes some of the same elements at depicted in FIGS. 1A and 1B, which bear like reference numerals. For example, tip 14 includes tip shell 42, which connects to catheter body 34; transducer 16 is mounted on attenuative backer 44; and fluid, such as saline S, is discharged from tip 14 through appropriate porting. However, tip shell 42 of FIG. 2A includes three sections 50A, 50B and 50C that are formed by two springs 52A and 52B. Spring 52A separates tip shell 42 into distal portion 50A and middle portion 50B, while spring 52B separates tip shell 42 into middle portion 50B and proximal portion 50C.

Target 49A and spring 52A are paired to provide an echo waveform that is predominantly an indication of axial movement of section 50A relative to section 50B. Target 49B and spring 52B are paired to provide a separate (in time) echo waveform that is predominantly an indication of bending movement of section 50B relative to section 50C. As such, to the extent possible, spring 52A is configured to have a stiffer bending spring constant than axial spring constant in order to primarily permit axial movement of spring 52A. Conversely, spring 52B is oppositely configured to have a stiffer axial spring constant than bending spring constant in order to primarily permit bending movement of spring 52B. However, more importantly, the shape of targets 49A and 49B are optimized to provide echo waveforms that predominantly respond to changes in axial compression or bending, respectively. Targets 49A and 49B may be formed of reflective metal and backed with a microsphere-filled polymer, or any other suitable material.

Target 49B comprises a ring-shaped body having planar surface 54 that is disposed a predetermined distance from transducer 16. Target 49B is disposed concentrically around centerline CL and may comprise a polished metallic, for example, ring having a uniform cross-section as revolved around centerline CL. Thus, target 49B may be joined to section 50B around its three-hundred-sixty-degree circumference. Alternatively, target 49B may be mounted to segment 50B with projections, in a similar fashion as target 18 can be mounted to tip shell 42 as described with reference to FIG. 1B, to allow fluid and wiring to pass around target 49B. Planar surface 54 is disposed approximately parallel to emitting surface 48 of transducer 16 when spring 52B is at rest. As such, planar surface 54 will form an ever-increasing angle with emitting surface 48 of transducer 16 as spring 52B bends. Thus, in an un-deflected state, as shown in FIG. 2A, ping $P_1$ from transducer 16 travels to, and returns from, surface 54 along a straight line. Target 49B includes center bore 56, which allows ping $P_2$ for target 49A to pass through target 49B. Note especially that the $P_1$ echo will be returned earlier and separately in time than the later $P_2$ echo.

Target 49A includes curved reflection surface 58 that is disposed a predetermined distance from transducer 16. Target 49A may be mounted to tip shell 42 in any suitable fashion. In one embodiment, target 49A comprises a portion of a ball or sphere, and the curvature of surface 58 is uniform about centerline CL of tip 14. The curvature of surface 58 may, however, have other non-circular geometries based on other factors, such as the stiffness of spring 52A. For target 49A, the curvature of surface 58 is correlated to the bending stiffness of spring 52B such that, as spring 52B deflects, surface 58 presents a small arcuate segment having a theoretical tangent surface that will always be parallel to emitting surface 48 of transducer 16 at centerline CL. Thus, in an un-deflected state, as shown in FIG. 2A, ping $P_2$ from transducer 16 travels to, and returns from, surface 58 along a straight line.

Figure 2B:
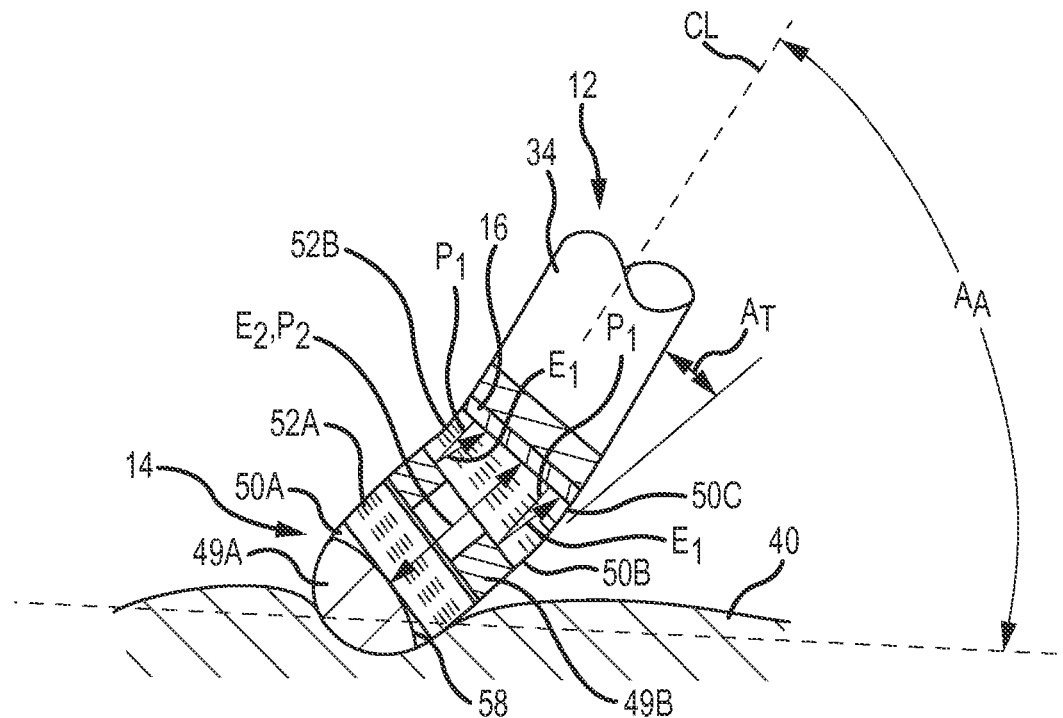
FIG. 2B is a schematic diagram of the ablation catheter of FIG. 2A illustrating the force-sensing tip being deflected via contact with tissue so as to change positions of a spherical target and a planar target relative to an acoustic transducer.

FIG. 2B is a schematic diagram of ablation catheter 12 of FIG. 2A illustrating force-sensing tip 14 being deflected via contact with tissue 40 so as to change a position of targets 49A and 49B relative to acoustic transducer 16. FIG. 2B includes the same elements as shown in FIG. 2A, but tip 14 contacts tissue 40 at approach angle $A_A$ to cause deflection of tip 14 an amount equivalent to tilt angle $A_T$.

As discussed above, planar surface 54 is disposed approximately parallel to emitting surface 48 of transducer 16 such that planar surface 54 will form an ever-increasing angle with emitting surface 48 of transducer 16 as spring 52B bends. Thus, ping $P_1$ is deflected back to transducer 16 as echo $E_1$ at an angle. Because echo $E_1$ has a ring shape due to the ring shape of target 49B, the average phase change of echo $E_1$ will be approximately zero, thus giving rise to an overall echo having the same phase as the un-deflected tip of FIG. 2A. However, the intensity of echo $E_1$ will change as more of ping $P_1$ is deflected off of transducer 16. For example, the upper portion of echo $E_1$ in FIG. 2B will be deflected toward centerline CL such that transducer 16 will still register most if not all of the upper portion of echo $E_1$. However, the lower portion of echo $E_1$ in FIG. 2B will be deflected away from centerline CL such that transducer will only partially register the lower portion of echo $E_1$. Thus, the total intensity of echo $E_1$ will drop. Because the angular displacement of target 49B will dominate the change of echo $E_1$ (because echo $E_2$ hasn't happened yet and because spring 52B has high axial stiffness), axial displacement of spring 52B can be ignored. Furthermore, movement of spring 52A will have no influence on echo $E_1$. Echo $E_1$ is therefore used to primarily provide an indication of bending force applied to tip 14.

As mentioned above, the curvature of surface 58 is shaped such that a small arcuate segment of surface 58 will always form a theoretical tangent plane that is parallel to emitting surface 48 of transducer 16 at centerline CL for a modest bend angle range. Thus, ping $P_2$ is deflected back to transducer 16 as echo $E_2$ along substantially the same path that ping $P_2$ took to travel to target 49B for any designed bending position of spring 52B. This is made possible by the relationship of the curve of surface 58 and the bending stiffness of spring 52B. Thus, echo $E_2$ will primarily register phase-shifting from axial displacement of target 49A due to compression or tension of spring 52A. Bending of spring 52A can be minimized by having the bending spring constant of spring 52A be much stiffer than the bending spring constant of spring 52B. Echo $E_2$ is therefore used to primarily provide an indication of axial force applied to tip 14.

Figure 2C:
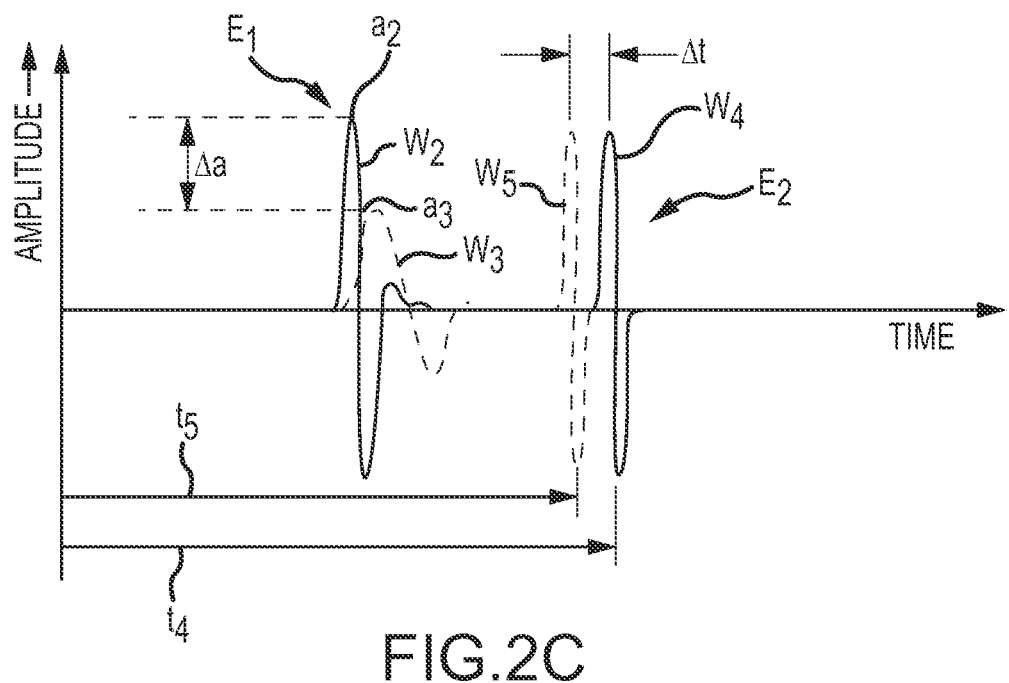
FIG. 2C is a graph illustrating the behavior of pulse-echo waveforms from the acoustic transducer of FIGS. 2A and 2B before and after deflection of the acoustic targets.

FIG. 2C is a graph illustrating the behavior of the waveforms for echoes $E_1$ and $E_2$ from acoustic transducer 16 before and after deflection of force-sensing tip 14.

Waveform $W_2$ depicts echo $E_1$ (FIG. 2B) for tip 14 under no load, such as would be generated in FIG. 2A. Waveform $W_3$ depicts echo $E_1$ for tip 14 under axial and bending load, such as would be generated in FIG. 2B. Waveform $W_2$ is the baseline of echo $E_1$ received by transducer 16 for ping $P_1$ generated by transducer 16 for a given set of inputs from acoustic energy driver 24. Waveform $W_2$ has a given amplitude $a_2$, while waveform $W_3$ has a given amplitude $a_3$.

Waveform $W_4$ depicts echo $E_2$ (FIG. 2B) for tip 14 under no load, such as would be generated in FIG. 2A. Waveform $W_5$ depicts echo $E_2$ for tip 14 under axial and bending load, such as would be generated in FIG. 2B. Waveform $W_4$ is the baseline of echo $E_2$ received by transducer 16 for ping $P_2$ generated by transducer 16 for a given set of inputs from acoustic energy driver 24. Waveform $W_4$ has a given phase $t_4$, while waveform $W_5$ has a given phase $t_5$.

As can be seen in FIG. 2C, echo $E_1$ shifts from waveform $W_2$ to waveform $W_3$ as the total energy from ping $P_1$ reflected back to transducer 16 is reduced when tip 14 is bent. As explained above, tilting of target 49B reflects more of the energy from ping $P_1$ off of transducer 16, resulting in a loss of detected energy. Thus, echo $E_1$ experiences an amplitude reduction $\Delta a$ from $a_2$ to $a_3$. Waveform $W_3$ additionally experiences a waveform broadening as compared to waveform $W_2$ due to spreading of the energy from ping $P_1$ across transducer 16. However, echo $E_1$ will not experience any significant phase-shift as compared to the amplitude change. In any event, the embodiment of force-sensing tip 14 of FIGS. 2A and 2B has a separate axial force sensing arrangement such that analysis of waveform $W_2$ and $W_3$ for axial force is unnecessary.

As can be seen in FIG. 2C, echo $E_2$ shifts from waveform $W_4$ to waveform $W_5$ as the total time for ping $P_2$ to be reflected back to transducer 16 is reduced when tip 14 is axially translated. Thus, echo $E_2$ will experience a phase shift $\Delta t$ from $t_4$ to $t_5$ to the left in FIG. 2C. As explained above, axial displacement of target 49A reflects the same amount of the energy from ping $P_2$ off of transducer 16 due to the curvature of surface 58, regardless of the bending incurred at spring 52B. Thus, the resulting amplitudes of waveforms $W_4$ and $W_5$ are the same. Waveforms $W_4$ and $W_5$ will provide an indication of the total axial displacement of target 49A due to axial changes in springs 52A and 52B.

The various embodiments described with reference to FIGS. 2A-2C provide decoupled axial force and bending force measurements to analyzer 22 (FIG. 1A). As such, as described above, each measurement is optimized to provide higher resolution or accuracy for one desired parameter. Specifically, waveform $W_2$ and $W_3$ can be analyzed only for phase shifting to determine axial force, while waveforms $W_4$ and $W_5$ can be analyzed only for amplitude changes to determine bending force.

Figure 3A:
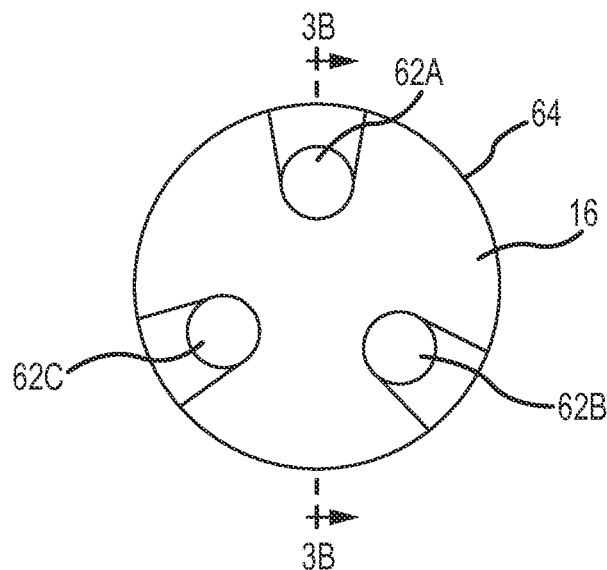
FIG. 3A is an axial view of another embodiment of an ablation catheter having three acoustic targets spaced around an interior circumference of a catheter tip.
Figure 3B:
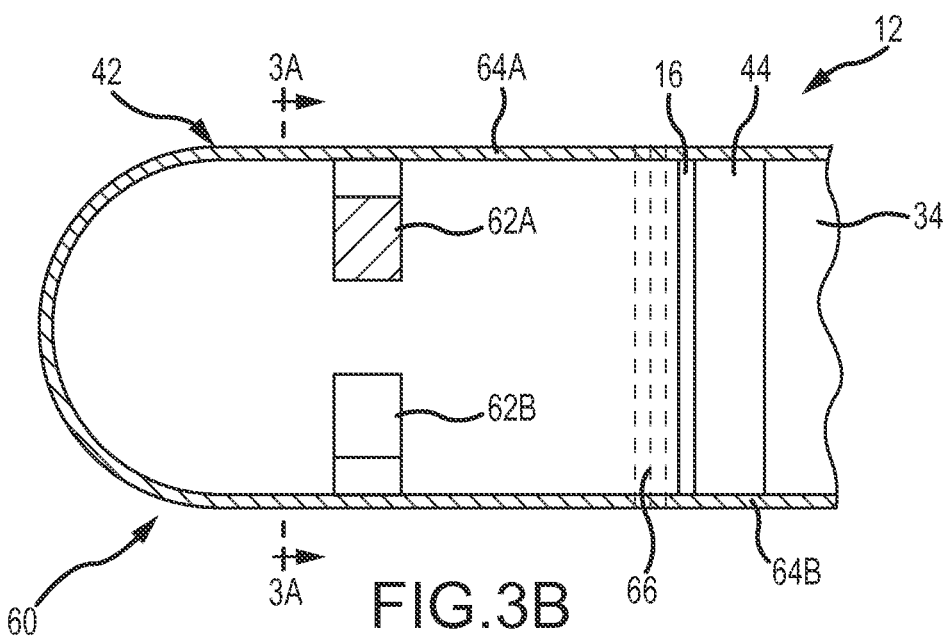
FIG. 3B is section 3B-3B of FIG. 3A illustrating the position of the three acoustic targets relative to an acoustic transducer.

FIG. 3A is an axial view of another embodiment of ablation catheter 12 having force-sensing tip 60 with three acoustic targets 62A, 62B and 62C angularly and radially spaced around an interior circumference of tip shell 42. FIG. 3B is section 3B-3B of FIG. 3A and illustrates the axial position of acoustic targets 62A-62C relative to acoustic transducer 16. FIGS. 3A and 3B are discussed concurrently. In the depicted embodiment, targets 62A-62C are spaced equally one-hundred-twenty degrees apart around tip shell 42 in the same plane.

Tip shell 64 is connected to catheter body 34 via spring 66 to produce distal section 64A and proximal section 64B. Transducer 16 is mounted on attenuative backer 44 within tip shell 42. Transducer 16 and targets 62A-62C operate in much the same way as transducer 16 and target 49B in FIG. 2B. However, targets 62A-62C will present transducer with three distinct echoes, as compared to a single echo from target 49B. In an un-deflected state, the echoes will present transduce 16 with a unified waveform. Similarly, under a pure axial displacement of spring 66 the echoes will present transducer 16 with the same waveform as the un-deflected state, but shifted in time. However, bending of spring 66 will provide three distinct waveforms to analyze. In particular, the waveforms will have different phase (i.e. time delay), and will all experience peak broadening with a total intensity drop, as shown in FIG. 3C.

Figure 3C:
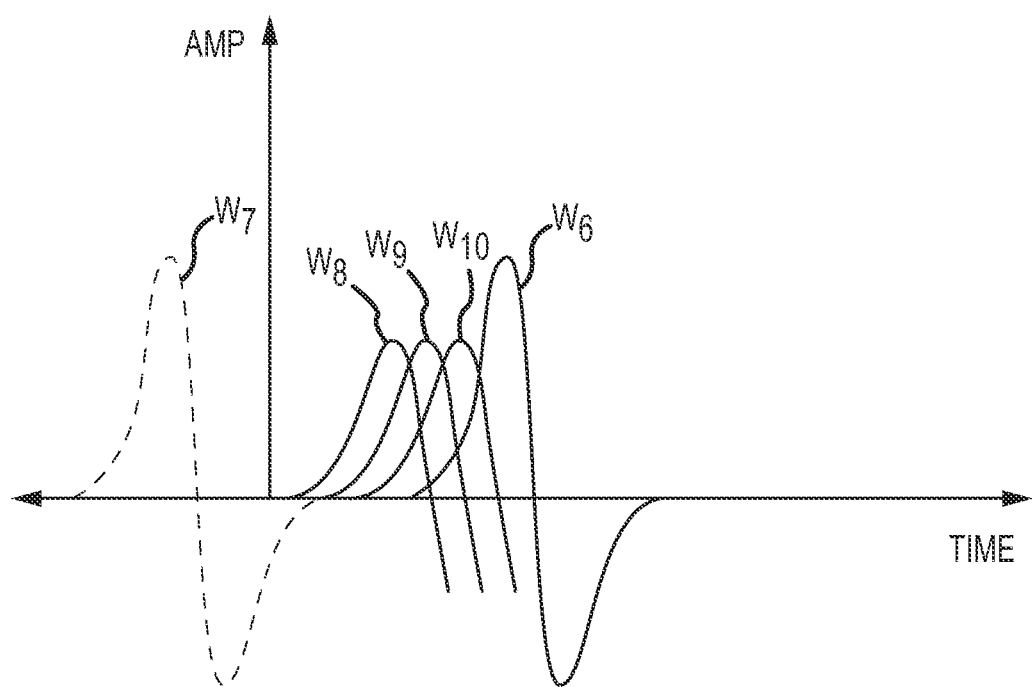
FIG. 3C is a graph illustrating the behavior of pulse-echo waveforms of the force-sensing tip of FIGS. 3A and 3B before and after deflection of the three acoustic targets.

FIG. 3C is a graph illustrating the behavior of waveforms $W_6$-$W_{10}$ for a ping echo from transducer 16 for force-sensing tip 14 of FIGS. 3A and 3B. Waveform $W_6$ is the baseline of the echo received by transducer 16 for a ping generated by transducer 16 for a given set of inputs from acoustic energy driver 24 (FIG. 1A). Waveform $W_7$ illustrates the change in waveform $W_6$ for a pure axial displacement of spring 66 (FIG. 3B). Waveforms $W_8$-$W_{10}$ illustrate the change in waveform $W_6$ for a bending displacement of spring 66.

As mentioned above, if spring 66 undergoes pure compression, the total energy reflected back to transducer 16 will remain the same, but the time it takes for that energy to return to transducer 16 will decrease. Thus, waveform $W_7$ indicates only a phase shift of waveform $W_6$. If spring 66 undergoes bending, the total energy reflected back to transducer 16 will drop. Thus, the sum under the curves of waveforms $W_8$-$W_{10}$ will be less than the sum under the curve of waveform $W_6$. In addition, due to the segregation of targets 62A-62C into three distinct bodies, three distinct waveforms will be reflected back to transducer 16, each undergoing an amplitude reduction and a peak broadening from waveform $W_6$.

If spring 66 undergoes combined axial and bending displacement, waveform 6 would change into three shorter and broadened waveforms that are shifted in time. The embodiment of FIGS. 3A-3C is useful in providing both axial and bending information with three separate signals, thus making identification of axial and bending displacement easier to identify and analyze.

Figure 4A:
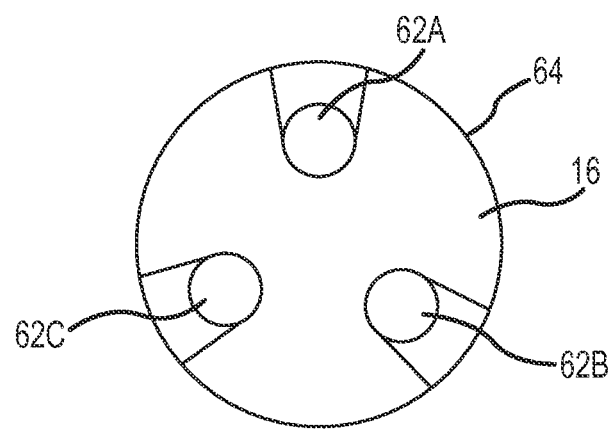
FIG. 4A is an axial view of another embodiment of an ablation catheter having three acoustic targets spaced at different axial and radial positions along a length of the catheter tip.
Figure 4B:
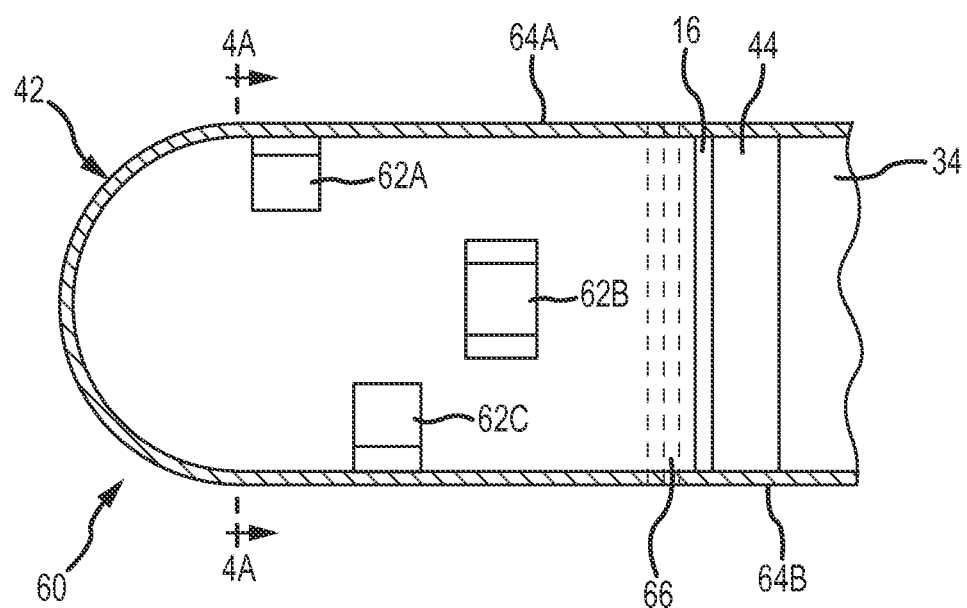
FIG. 4B is a schematic representation of the side of the ablation catheter of FIG. 4A illustrating the position of the three acoustic targets relative to an acoustic transducer.

FIG. 4A is an axial view of another embodiment of ablation catheter 12 having force-sensing tip 60 with three acoustic targets 62A, 62B and 62C angularly and radially spaced around an interior circumference of tip shell 42 at three different axial positions along a length of tip shell 42. FIG. 4B is a diagram illustrating the axial positions of acoustic targets 62A-62C relative to acoustic transducer 16. FIGS. 4A and 4B are discussed concurrently. In the depicted embodiment, targets 62A-62C are angularly spaced equally one-hundred-twenty degrees apart around tip shell 42. As such, the embodiment of FIGS. 4A and 4B is configured the same as the embodiment of FIGS. 3A and 3B, but for the differing axial positions of targets 62A-62C.

The embodiment of FIGS. 4A and 4B improves upon the embodiment of FIGS. 3A and 3B by making it clear how each of the three acoustic targets 62A-62C moves and which echo belongs to each target. Thus, improvement over reporting only the angular deflection force magnitude can be achieved by reporting both the angular force magnitude and the angular force angular direction, if that is desired. Thus, as with FIGS. 3A and 3B, bending of spring 66 will produce three echo waveforms. However, with the embodiment of FIGS. 4A and 4B, the axial position of each of the waveforms will be different such that axial displacement of spring 66 produces three distinct waveform displacements. In essence, the embodiment of FIGS. 4A and 4B provides three separate echoes and waveforms that will exhibit distinct, non-overlapping phase changes and amplitude changes for axial and bending displacement of spring 66.

Figure 4C:
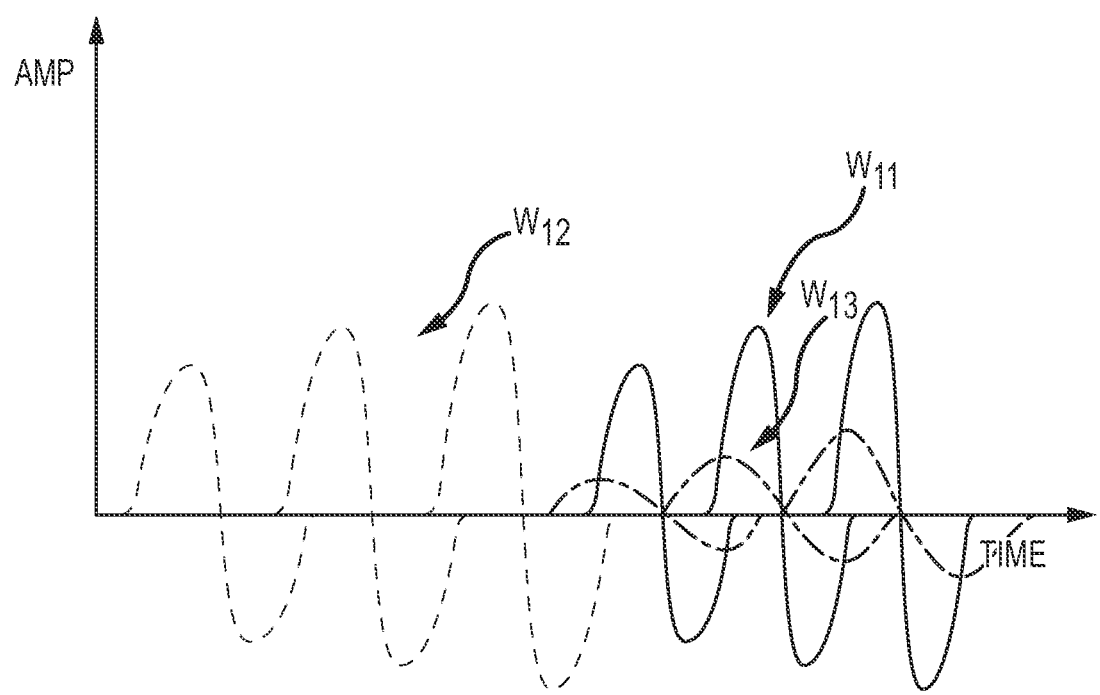
FIG. 4C is a graph illustrating the behavior of pulse-echo waveforms of the force-sensing tip of FIGS. 4A and 4B before and after simultaneous deflection of the three acoustic targets.

FIG. 4C is a graph illustrating the behavior of waveform groups $W_{11}$, $W_{10}$ and $W_{12}$ for ping echoes from transducer 16 for force-sensing tip 14 of FIGS. 4A and 4B. Waveform group $W_{11}$, shown in solid lines, illustrates the baseline echo for each of targets 62A-62C for an un-deflected tip 14. Waveform group $W_{12}$, shown in dashed lines, illustrates the echo for each of targets 62A-62C for axial displacement of spring 66 (FIG. 3B). Waveform group $W_{13}$, shown in dotted lines, illustrates the echo for each of targets 62A-62C for bending displacement of spring 66. As can be seen in FIG. 4C, targets 62A-62C provide three separate signals that can each be measured for amplitude and phase-shift, thus giving rise to six separate indicators of the axial and bending force applied to tip 14.

Figure 5:
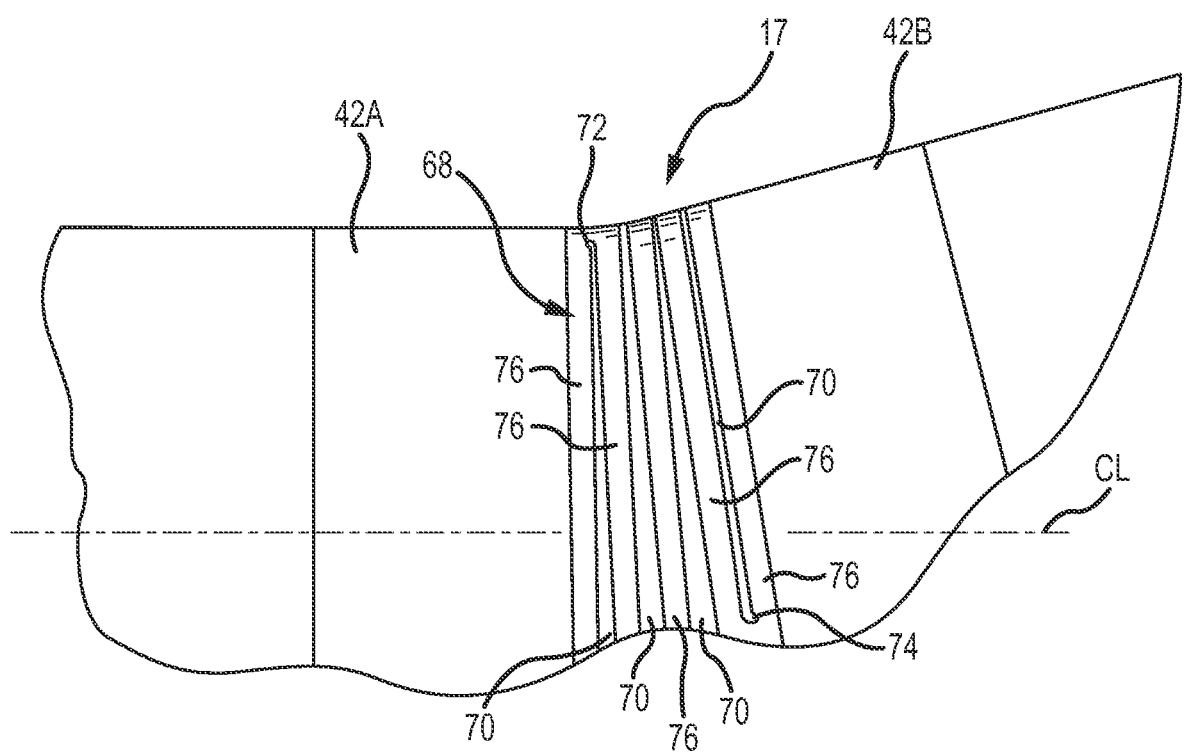
FIG. 5 is a side view of a force-sensing tip having a helical spring joining distal and proximal portions of a tip shell.

FIG. 5 is a side view of force-sensing tip 14 of FIG. 1B having spring 17 disposed between distal section 42A and proximal section 42B of tip shell 42. In the illustrated embodiment, spring 17 comprises a helical spring 68 integrally formed from tip shell 42, thereby joining sections 42A and 42B.

Helical spring 68 may be laser-formed into tip shell 42. For example, spring 68 comprises incision 70 that begins at point 72 and terminates at point 74. Incision 70 travels a spiral or helical path between points 72 and 74. In the depicted embodiment, incision 70 traverses the circumference of tip shell approximately three and a quarter times, thereby forming three and a quarter coils 76. Incision 70 is narrow and traverses only a small axial extent of tip shell 42 to minimize invasiveness in tip 14. In one embodiment, incision 70 extends all the way through, e.g. radially through, tip shell 42 to allow fluid within tip 14 to escape, such as to provide irrigation of tip 14 during an ablation process.

The particular width of incision 70, the thickness of coils 76, and the number of coils 76 can be configured to give spring 68 desired axial and bending spring constants $k_a$ and $k_b$. The spring constants, which may be determined by experimentation, are stored in control unit 30 (FIG. 1A) in order to allow analyzer 22 to perform force calculations based on distance calculations determined from echo waveform analysis. For example, the distance D that target 18 (FIG. 1A) is axially traversed can be determined knowing the speed (wavelength) of the echo and the associated time reduction (phase-shift) in the return of the echo using the simple equation D=v*t, where D is distance, v is velocity and t is time. Thereafter, with reference to Hooke's Law, D can be substituted for X, and can be used with the determined spring constant $k_a$ to calculate the axial force $F_A$ applied to tip 14. A similar analysis can be performed for determining the bending force.

Although spring 17 is illustrated as a helical spring, other types of springs may be used. In one embodiment, spring 17 may comprise a laser etching of tip shell 42 that simply weakens the material of tip shell 42 without penetrating all the way through tip shell 42. In other embodiments, wave springs, Belleville springs, normally closed tension springs, normally open compression or tension springs, coil springs, garter springs, elastomeric springs or pads, pressurized bladder springs or pads, and the like may be used.

Furthermore, tip 14 can be provided with hard stops that limit deflection of spring 17. In particular, it is desirable to limit bending of spring 17 to prevent echoes from being aimed off of transducer 16, overstressing of spring 17, the over-application of force to tip 14, and the like. In one embodiment, a stop may comprise multiple bodies, such as rubber inserts, positioned into incision 70 between coils 76 to limit the spring-action of spring 17. In another embodiment, a stop may comprise a strap positioned inside tip shell 42 that extends between sections 42A and 42B to limit bending.

Figure 6:
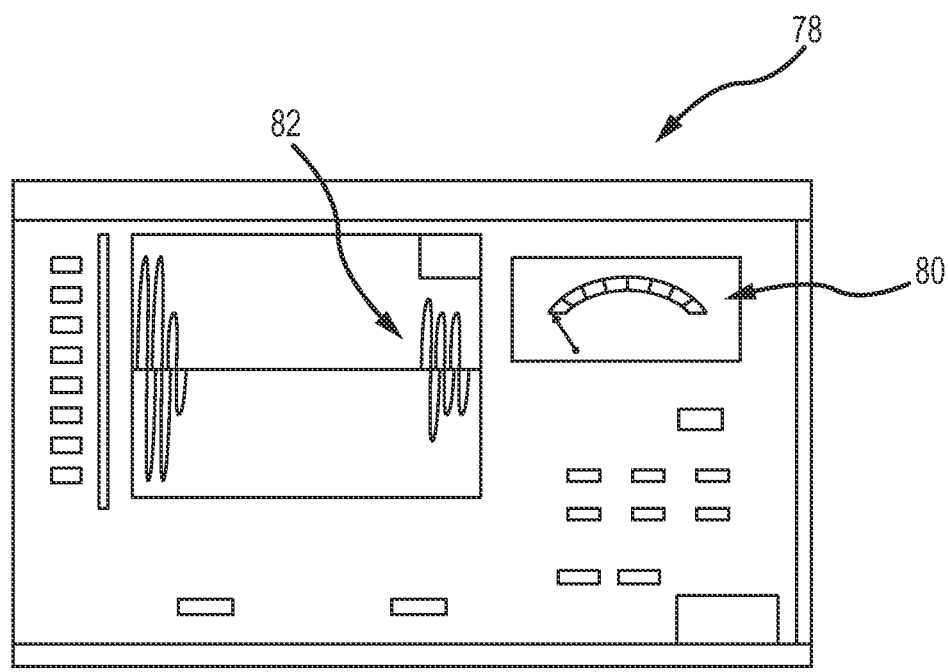
FIG. 6 is a schematic representation of a graphical user interface for a medical device system showing an indicator for force sensed by a force-sensing tip for a catheter and an acoustic waveform generated by the force-sensing tip.

FIG. 6 is a schematic representation of graphical user interface (GUI) 78 for medical device system 10 (FIG. 1A) showing force indicator 80 and echo waveform indicator 82. GUI 78 may be located within user interface 32 of FIG. 1A. GUI may comprise any suitable display, such as a liquid crystal (LCD) display or light emitting diode (LED) display, that can interface with control unit 30, which may comprise a computer of known construction. It should be noted that the contents on the display can be easily modified and the specific data presented is illustrative and not limiting of the invention.

GUI 78 is used to show data to an operator of system 10 and to present certain options that allow the user to tailor system configuration for a particular use. In the illustrated embodiment, GUI 78 shows force indicator 80 as a graphical dial having a needle that provides an indication of force. For example, the dial may indicate less force at the left end, and more force at the right end. The dial may include graduation marks to indicate force in increments of grams or any other force unit. Alternatively, the dial may be color coded to show force, e.g. yellow to show force insufficient for ablation, green to show acceptable force, and red to show an undesirable amount of force. In alternative embodiments, force indicator 80 may comprise a digital force readout, or any other analog or digital display. Note that only one force meter is shown in FIG. 6. This could indicate the vector sum of the axial and bend force components, for example. Likewise, the force meter may show separately the axial and bend force components with more than one readout meter or icon. The ablation generator may be enabled by the achievement of a recommended minimum force for good efficacy. The irrigation fluid pump may provide enough water (saline) for force sensing and then up the flow rate while RF ablation takes place.

Echo waveform indicator 82 is used to show waveforms generated by transducer 16 and any of the various targets described herein. Echo waveform indicator 82 may be selected as an optional output, as operators of system 10 typically need only to know the magnitude of the total force applied by tip 14 to conduct the desired procedures. However, it may be useful in some circumstances, such as for troubleshooting, to see the raw waveforms generated by transducer 16. Echo waveform indicator 82 typically provides a horizontal time axis and a vertical amplitude axis that provides an indication of the magnitude of intensity of an echo, the speed of the echo and the like.

The embodiments of force-sensing tips for use with catheters described herein provide advantages and benefits over other types of force-sensing tips. For example, the force-sensing tips of the present disclosure are able to provide accurate force measurements for both axial and bending force applied to or by a catheter tip. The force-sensing tips can be incorporated into existing catheter tips without impacting performance of other catheter functions, or significantly changing the size and operation of the catheter tip. Additionally, the present force-sensing tips are self-contained and do not require other external systems to interact with the catheter tip to determine displacement of the tip. Furthermore, the force-sensing tips can be configured to provide multiple data channels to provide redundancy and enhance resolution of obtained data.

Although at least one embodiment of a force-sensing tip for a catheter has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A force-sensing tip assembly for a catheter, the force-sensing tip assembly comprising:
    a tip shell;
    an acoustic transducer disposed within the tip shell, the acoustic transducer capable of generating an acoustic ping;
    a first target spaced from the acoustic transducer within the tip shell; and
    a first spring in the tip shell, the first spring configured to allow a relative position between the acoustic transducer and the first target to change over a range; wherein the first target is shaped and positioned to reflect at least a portion of the acoustic ping back to the acoustic transducer as a first echo over at least a portion of the range;
    wherein the first echo provides a combined indication of changes in both axial and bending positions of the first target relative to the acoustic transducer.

2. The force-sensing tip assembly of claim 1, wherein the range includes a range of axial positions and a range of bending positions.

3. The force-sensing tip assembly of claim 1, and further comprising:
    a fluid path within the tip for acoustic energy to travel between the transducer and the first target in either direction.

4. The force-sensing tip assembly of claim 1, wherein the first spring comprises an incision in the tip shell that forms a spring which allows one or both of a hinging deflection and an axial deflection.

5. The force-sensing tip assembly of claim 1, wherein the first target includes a planar surface disposed approximately parallel to an emitting surface of the acoustic transducer when the spring is at rest.

6. The force-sensing tip assembly of claim 5, wherein the planar surface is configured to reflect the first echo back to the acoustic transducer at an angle relative to the emitting surface when a bending force is applied to the first spring.

7. The force-sensing tip assembly of claim 1, wherein the first target includes a curved surface facing towards an emitting surface of the acoustic transducer.

8. The force-sensing tip assembly of claim 7, wherein the curved surface is configured to reflect the first echo back to the transducer along the same path the acoustic ping took to the first target for an entirety of a bending range of the tip shell.

9. The force-sensing tip assembly of claim 7, wherein the curved surface is configured to reflect the first echo back to the transducer with approximately the same waveform amplitude when a bending force is applied to the first spring.

10. The force-sensing tip assembly of claim 1, and further comprising:
    a second target disposed within the tip shell, the second target having a different surface geometry than the first target.

11. The force-sensing tip assembly of claim 1, and further comprising:
a second target disposed within the tip shell, the second target having a different axial position than the first target.

12. The force-sensing tip assembly of claim 1, and further comprising:
a second target disposed within the tip shell, the second target having a different circumferential or radial position than the first target.

13. The force-sensing tip assembly of claim 1, and further comprising:
a second target disposed within the tip shell, the second target configured to provide a second echo;
wherein the first echo and the second echo provide uncoupled indications of changes in axial position and bending position of the first target and second target relative to the acoustic transducer, respectively.

14. The force-sensing tip assembly of claim 1, and further comprising:
a second target disposed within the tip shell, the second target configured to provide a second echo; and
a second spring joined to the tip shell;
wherein the first spring is stiffer than the second spring in the axial direction; and
wherein the second spring is stiffer than the first spring in the bending direction.

15. The force-sensing tip assembly of claim 1, and further comprising:
a second target disposed within the tip shell, the second target configured to provide a second echo;
wherein the first target comprises a curved surface facing towards an emitting surface of the acoustic transducer, the curved surface and the acoustic transducer extending through a centerline of the tip shell; and
wherein the second target comprises a ring shaped body having a planar surface disposed approximately parallel to the emitting surface of the acoustic transducer when the first spring is at rest, the ring shaped body configured to circumscribe the centerline of the tip shell.

16. The force-sensing tip assembly of claim 15, and further comprising:
a second spring joined to the tip shell;
wherein the first spring is configured to have a stiffer bending spring constant than an axial spring constant; and
wherein the second spring is configured to have a stiffer axial spring constant than a bending spring constant.

17. The force-sensing tip assembly of claim 15 wherein the first target is located proximate a closed end of the tip shell, and the second target is located proximate an open end of the tip shell.

18. A medical device system comprising:
a catheter shaft having a proximal region and a distal region;
a force-sensing tip assembly disposed at the distal region of the catheter shaft, the force-sensing tip assembly comprising:
a tip shell joined to the catheter shaft;
an acoustic transducer disposed within the tip shell, the acoustic transducer capable of generating and receiving an acoustic ping;
a first target spaced from the acoustic transducer within the tip shell to reflect the acoustic ping as a first reflected acoustic echo back to the acoustic transducer, the first reflected acoustic echo indicative of axial and bending displacement of the first target relative to the acoustic transducer; and
a first spring joined to the tip shell and configured to allow a relative position and tilt angle between the acoustic transducer and the first target to change by deflection of the spring; and
a control system connected to the force-sensing tip via the catheter shaft, the control system configured to analyze changes in the first reflected acoustic echo, associated with the axial and bending displacement of the first target relative to the acoustic transducer, to determine a force generated by the first spring.

19. The medical device system of claim 18, wherein:
the first target includes a planar surface disposed approximately parallel to an emitting surface of the acoustic transducer when the spring is at rest; and
the axial displacement of the first target relative to the acoustic transducer associated with an echo delay of the first reflected acoustic echo, and the bending displacement associated with an echo broadening of the first reflected acoustic echo.

20. The medical device system of claim 18, and further comprising:
a second target disposed within the tip shell at a different axial position than the first target and configured to deflect the acoustic ping as a second reflected acoustic echo back to the acoustic transducer; and
a second spring joined to the tip shell at a different axial position than the first spring.

21. The medical device system of claim 20, wherein:
the first target includes a planar surface facing towards an emitting surface of the acoustic transducer when the spring is at rest;
the second target includes a curved surface facing towards the emitting surface of the acoustic transducer for all positions of the spring; and
the first and second reflected acoustic echoes provide an uncoupled indication of axial and bending displacement of the tip shell.

22. An ablation catheter comprising:
a catheter shaft;
a flexible tip coupled to the catheter shaft;
a transducer disposed within the flexible tip to remain stationary with the shaft;
a target disposed within the flexible tip to move relative to the shaft when the flexible tip bends;
a fluid path between the transducer and the target to allow passage of a transducer ping and its respective reflected echo; and
wherein the target is configured to provide the transducer with an echo that corresponds to a position and angle of the flexible tip relative to the shaft.

* * * * *